United States Patent [19]
Stout

[11] Patent Number: 5,981,296
[45] Date of Patent: *Nov. 9, 1999

[54] STABILIZATION OF PARTICLE REAGENTS

[75] Inventor: Richard Wayne Stout, Wilmington, Del.

[73] Assignee: Dade Behring Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/801,878

[22] Filed: Feb. 18, 1997

[51] Int. Cl.$^6$ .................... G01N 33/53; G01N 33/566; G01N 33/546
[52] U.S. Cl. .................. 436/501; 436/533; 436/500; 436/815; 436/534
[58] Field of Search .................... 436/501, 533, 436/500, 815, 534; 530/350

[56] References Cited

U.S. PATENT DOCUMENTS

| | | | |
|---|---|---|---|
| 4,101,549 | 7/1978 | Focella et al. | 544/301 |
| 4,226,747 | 10/1980 | Roncari | 260/8 |
| 4,233,286 | 11/1980 | Soothill et al. | 424/12 |
| 4,351,824 | 9/1982 | Lehrer | 424/12 |
| 4,401,765 | 8/1983 | Craig et al. | 436/533 |
| 4,408,008 | 10/1983 | Markusch | 524/591 |
| 4,415,700 | 11/1983 | Batz et al. | 524/548 |
| 4,426,485 | 1/1984 | Hoy et al. | 524/591 |
| 4,427,781 | 1/1984 | Masson et al. | 436/509 |
| 4,427,836 | 1/1984 | Kowalski et al. | 525/301 |
| 4,480,042 | 10/1984 | Craig et al. | 436/533 |
| 4,510,019 | 4/1985 | Bartelloni | 162/141 |
| 4,581,337 | 4/1986 | Frey et al. | 436/533 |
| 4,582,810 | 4/1986 | Rosenstein | 436/528 |
| 4,594,363 | 6/1986 | Blankenship et al. | 521/64 |
| 4,784,912 | 11/1988 | Schaeffer et al. | 428/402 |
| 4,837,168 | 6/1989 | de Jaeger et al. | 436/533 |
| 4,885,350 | 12/1989 | Yamashita et al. | 526/201 |
| 4,902,500 | 2/1990 | Jansen et al. | 424/78 |
| 4,910,229 | 3/1990 | Okubo | 521/72 |
| 4,929,662 | 5/1990 | Hogenmuller et al. | 524/376 |
| 4,952,622 | 8/1990 | Chauvel et al. | 524/376 |
| 5,061,766 | 10/1991 | Yamashita et al. | 526/191 |
| 5,109,038 | 4/1992 | Chauvel et al. | 523/207 |
| 5,124,245 | 6/1992 | Cummins et al. | 435/5 |
| 5,136,027 | 8/1992 | Pope | 530/427 |
| 5,157,084 | 10/1992 | Lee et al. | 525/301 |
| 5,166,077 | 11/1992 | Kihara et al. | 436/534 |
| 5,210,039 | 5/1993 | Cummins et al. | 436/17 |
| 5,248,620 | 9/1993 | Sluka et al. | 436/531 |
| 5,252,459 | 10/1993 | Tarcha et al. | 435/6 |
| 5,336,621 | 8/1994 | Primes et al. | 436/534 |
| 5,521,253 | 5/1996 | Lee et al. | 525/301 |

FOREIGN PATENT DOCUMENTS

| | | |
|---|---|---|
| 0 134 660 | 3/1985 | European Pat. Off. |
| 0 318 081 | 5/1989 | European Pat. Off. |
| 0 727 663 | 8/1996 | European Pat. Off. |
| 35 24 179 A1 | 1/1986 | Germany |

*Primary Examiner*—Lynette F. Smith
*Assistant Examiner*—Brett Nelson
*Attorney, Agent, or Firm*—Leland K Jordan; Lois K Ruszala

[57] ABSTRACT

Stabilized particle reagents suitable for use in turbidimetric immunoassays are disclosed. The stabilized particle reagents contain functionalized polymer particles in which the surface of the particle has been modified with a molecular surface modifier having the structure:

$$R(OCH_2CH_2)_nNH_2$$

in which: R is —H, —CH$_3$ or —CH$_2$CH$_3$, and n is an integer between 2 and 10, inclusive. The stabilized particle reagents are resistant to premature or spontaneous aggregation during preparation or storage.

35 Claims, No Drawings

STABILIZATION OF PARTICLE REAGENTS

FIELD OF THE INVENTION

This invention relates to particle reagents for use in turbidimetric immunoassays. More particularly, this invention relates to particle reagents containing functionalized polymer particles that are resistant to premature or spontaneous aggregation during preparation and storage. Molecular surface modifiers are used in the preparation of the functionalized polymer particles.

BACKGROUND OF THE INVENTION

Agglutination, the reaction of bivalent antibodies with multivalent antigens to produce aggregates that can be detected and measured in various ways, has long been used to detect and quantify a wide variety of materials present in biological fluids. These materials, known generally as analytes, include drugs, drug metabolites, serum proteins, enzymes, and other materials of interest or clinical significance. With appropriate variations of the procedure either specific antigens or specific antibodies can be detected.

Increased sensitivity can be achieved by the use of particle reagents. A particle reagent typically consists of a latex particle containing an analyte, analyte derivative, or analyte analog on its surface. Although the analyte can be absorbed onto the surface of the latex particle, desorption during storage or use can produce variations in reagent properties that affect the sensitivity and reproducibility of the assay. Desorption problems can be overcome by covalently attaching an analyte, analyte derivative, or analyte analog to the surface of the particle. However, particle reagents in which the analyte, analyte derivative, or analyte analog is covalently attached to the surface of the particle can preaggregate during manufacture or not perform well in the intended assay. Preaggregation is an especially severe problem for particle reagents in which the covalently attached group is derived from a hydrophobic analyte.

To overcome the problem of preaggregation, functionalized polymer particles, in which the analyte, analyte derivative, or analyte analog is covalently attached to the surface of the particle by a hydrophilic linking agent, have been prepared. Hydrophilic diamines or polyamines have been used to attach groups that are either inherently amine-reactive or can be made amine-reactive by activation to epoxide-functionalized latex particles. Frey and Simons, U.S. Pat. No. 4,581,337, for example, disclose attachment of a theophylline derivative to epoxide-functionalized latex particles with hydrophilic diamine or polyamine linking agents.

The stability of the reagent is generally affected by several factors, including the amount of negative charge on the particle and the relative balance between hydrophilic and hydrophobic regions on the particle surface. Inclusion of excess hydrophilic diamine or polyamine during preparation of the functionalized polymer particle produces particles whose surface has been modified by reaction with the excess amine. Particle reagents containing these particles perform well in immunoassays, showing, for example, a rapid and precise agglutination rate when combined with an appropriate antibody.

In some cases, however, it is desirable to synthesize functionalized polymer particles from hydrophobic analytes that lack the amine-reactive functionality required for attachment by a hydrophilic diamine or polyamine linking agent. Particle reagents prepared with certain drugs or drug derivatives, particularly hydrophobic ones such as lidocaine, quinidine, procainamide, and derivatives of procainamide such as formyl procainamide, tend to aggregate during synthesis in the presence of excess hydrophilic diamine or polyamine, making them unusable in turbidimetric immunoassays. Thus, a need exists for stabilized polymer particles suitable for use in immunoassays that are not susceptible to premature aggregation.

SUMMARY OF THE INVENTION

In one embodiment the invention is a stabilized particle reagent comprising functionalized polymer particles that have been stabilized against premature aggregation. The functionalized polymer particle comprise:

(A) a polymer particle having an inner core and outer shell, wherein:
  (1) said core is a polymer having a refractive index of at least 1.54;
  (2) said shell comprises, in polymerized form:
    (a) an ethylenically unsaturated monomer having an amine-reactive functional group;
    (b) optionally, one or more other ethylenically unsaturated monomers in an amount sufficient to produce a water insoluble polymer; and
    (c) optionally, up to 10% by weight of a cross-linking monomer;
(B) a conjugate covalently attached to the surface of said polymer particle by said amine-reactive functional group; and
(C) at least one molecular surface modifier covalently attached to the surface of said polymer particle by said amine-reactive functional group, said molecular surface modifier having the structure:

$R(OCH_2CH_2)_nNH_2$ wherein R is —H, —CH$_3$ or —CH$_2$CH$_3$, and n is an integer from 2 to 10, inclusive; and
wherein said functionalized polymer particle has a diameter of 30 to 100 nm.

The conjugate can be an analyte, analyte derivative, or analyte analog, or it can be a linking group covalently attached to an analyte, analyte derivative, or analyte analog. In a preferred embodiment, the amine-reactive group is an epoxide. In a preferred embodiment, R is hydrogen and n is an integer from 2 to 6, more preferably, an integer from 3 to 5. In a preferred embodiment, the conjugate does not contain a linking group; the analyte, analyte derivative, or analyte analog is bonded directly to the polymer particle.

DETAILED DESCRIPTION OF THE INVENTION

This invention relates to a stabilized particle reagent for use in turbidimetric immunoassays. The particle reagent comprises polymer particles that are stabilized against premature aggregation by one or more covalently bonded molecular surface modifiers.

Polymer particle refers to the core/shell particle before attachment of the conjugate, the molecular surface modifier, or any other accessary molecule. Functionalized polymer particles refers to the polymer particles after attachment of the conjugate and the molecular surface modifier. Stabilized particle reagent refers to a colloidal suspension of functionalized polymer particles in a substantially aqueous medium.

Molecular Surface Modifiers

The molecular surface modifiers are compounds of the structure:

R(OCH$_2$CH$_2$)$_n$NH$_2$ in which R is —H, —CH$_3$ or —CH$_2$CH$_3$, and n is an integer from 2 to 10, inclusive.

A preferred R group is hydrogen. n is preferably an integer from 2 and 6, inclusive, more preferably, an integer from 3 and 5, inclusive. A preferred molecular surface modifier is 2-[2-(2-aminoethoxy)ethoxy]ethanol (MA-10). As described below, these compounds can be covalently bonded to the surface of polymer particles to produce functionalized polymer particles that are stabilized against premature aggregation.

The molecular surface modifiers can be prepared by procedures well-known to those skilled in the art. MA-10, for example, can be prepared by reaction of 2-[2-(2-chloroethoxy])ethoxy]ethanol with sodium azide in dimethyl formamide to form 2-[2-(2-azidoethoxy)-ethoxy]ethanol, which can be converted to MA-10 by reduction of the azido group by ammonium formate in the presence of a palladium on carbon catalyst.

Preparation of Polymer Particles

The polymer particle has an inner core and an outer shell. The outer shell contains an amine-reactive functional group suitable for covalent attachment of both the conjugate and the molecular surface modifier.

The light scattering properties of the particle reagent depend on several variables, most importantly size of the polymer particles, the refractive index of the core of the polymer particles, and the wavelength of light used for analysis. Thus, the selection of core material, particle size, and the wavelength of light used for detection of the agglutination reaction are important factors in optimizing assay sensitivity. Small particles with a high refractive index and a short analysis wavelength are preferred for maximum sensitivity.

To produce the signal changes required for turbidimetric detection of the agglutination reaction, polymer particles whose inner core has a $n_D$ (refractive index at the sodium D line, 569 nm) of not less than 1.54 are preferred. In addition, the core polymer must not absorb a significant amount of light at the wavelength chosen for analysis, typically about 340 nm. The preparation of particles that satisfy these requirements is described in Craig, U.S. Pat. No. 4,401,765, and Craig, U.S. Pat. No. 4,480,042, each of which is incorporated herein by reference.

The core polymer can be selected from a large group of materials with high refractive indices. Core polymers with high aromaticity and/or high atomic weight substituents are preferred over aliphatic polymers. A list of polymers with refractive indices greater than 1.54 is disclosed in Craig, U.S. Pat. No. 4,480,042, columns 5 and 6. The core can be a homopolymer or a copolymer. Mixtures of monomers may be used to produce the core, provided that the resulting copolymer has a refractive index greater than 1.54.

Polymerizable monomers than contain halides, aromatic, and/or hetroaromatic groups can be used to produce polymers with the desired refractive index. Because emulsion polymerization can produce polymer particles of uniform and controlled size, polymers than can be prepared by emulsion polymerization are preferred. Preferred monomers for core formation include styrene and 2-vinyl naphthalene.

The outer shell of the polymer particle can be prepared from a wide range of polymerizable monomers that have functional groups capable of reacting with the conjugate and the molecular surface modifier. Optionally, the shell can also contain other monomers, including the monomer or monomers used to prepare the core. The shell can be attached to the core either by graft polymerization of the shell monomers to the residual ethylenically unsaturated groups of the core polymer or the shell monomers can be polymerized around the core to form a contiguous shell.

The shell is comprised of a monomer that contains an amine-reactive functional group, such as epoxy, aldehyde, succinimidyl ester, or allylic or benzylic halogen. These groups are suitable for covalent attachment of both the conjugate and the molecular surface modifier. Monomers that contain either an epoxy group or a benzylic chlorine, such as glycidyl methacrylate, glycidyl acrylate, vinyl glycidyl ether, allyl glycidyl ether, and chloromethyl styrene, are preferred. Monomers that contain an epoxy group, which can be conveniently used for covalent attachment of haptens, antibodies, proteins, haptenprotein conjugates, and other compounds of biological interest, are more preferred. A preferred monomer epoxy-containing monomer is glycidyl methacrylate. Preparation of polymer particles that contain a poly(styrene) core and a poly(glycidyl methacrylate) shell is disclosed by Craig, U.S. Pat. No. 4,480,042, Examples 1, 2, and 4.

Staged emulsion polymerization can produce core/shell polymers with the desired refractive index. To obtain a polymer of the desired refractive index, it is preferred that the polymer shell not exceed about 10% by weight of the polymer particle, based on the total weight of the core and shell, exclusive of materials covalently bonded to the particle.

A convenient way to control the size of the polymer particles is to first prepare a seed emulsion, whose particle size can be controlled by the amount of surfactant used. After preparation of the seed emulsion, additional monomer and surfactant can be added at a controlled rate to increase the size of the particles in the emulsion.

It is preferred to carry the conversion of the core monomer (s) to substantial completion before the shell monomers are added to the polymerization to minimize the amount of core monomer(s) incorporated into the shell polymer. This produces a shell that is a homopolymer or copolymer of known composition rather than a polymer of unknown composition. Conversions in excess of 98% can be attained by increasing the temperature of the core emulsion to about 95° C. at the end of the polymerization. To further reduce the possibility of producing a particle whose surface is a copolymer of unknown composition, the shell monomer can be added gradually, rather than batchwise, so that any residual core monomer(s) are consumed during the early stages of shell polymer formation. When the shell monomer contains an epoxy group, the shell may comprise not more than 10% by weight of the core monomers.

To crosslink the shell, up to about 10% by weight, based on the weight of the shell, of a crosslinking monomer may be added to the polymerization. Crosslinking monomers contain two or more ethylenically unsaturated, polymerizable groups, such as ethylene-glycol diacrylate, ethyleneglycol dimethacrylate, diethyleneglycol dimethacrylate, diethyleneglycol diacrylate, triethyleneglycol diacrylate, and triethyleneglycol dimethacrylate. A preferred crosslinking monomer is ethyleneglycol dimethacrylate.

In general, polymer particles with a diameter of 30 to 100 nm can be used. Because of both increased slope sensitivity and faster reaction rate, polymer particles with a diameter of less than about 100 nm are preferred. For reasons of stability and synthetic convenience, polymer particles with a diameter of more then about 30 nm are preferred. More preferably the polymer particles have a diameter of 50 to 90 nm, still more preferably 60 to 80 nm. The most preferred particles have a diameter of about 75 mn.

Conjugates

The compound to be reacted with the polymer particle is known as the conjugate. It can be either an analyte, analyte derivative, or analyte analog; a functionalized derivative of an analyte, analyte derivative, or analyte analog, in which some modification has been made to introduce amine group that is reactive with the polymer particle; or an analyte, analyte derivative, or analyte analog covalently bonded to a linking group. In a preferred embodiment, the conjugate does not contain a linking group; the analyte, analyte derivative, or analyte analog is directly covalently bonded to the polymer particle. Analytes that contain amine functionality, such as lidocaine and procainamide, can be directly reacted with the polymer particle.

Conjugates can be derived from a wide variety of materials of biological interest. Such materials include, for example, serum, plasma, salivary, urinary, and milk proteins; drugs and drug metabolites; vitamins; hormones; enzymes; antibodies; polysaccharides; bacteria; protozoa; fungi; viruses; cell and tissue antigens; and other blood cell and blood fluid substances. Of special interest are various drugs and drug metabolites as well as substances for which a quantitative determination is required for the assessment of a disease state. Useful conjugates include lidocaine; procainamide; N-trifluoroacetyl procainamide; quinidine; cyclosporin; and amine conjugates of valproic acid, digoxin, and digoxigenin.

Linking Groups

The analyte, analyte derivative, or analyte analog may be covalently attached to a linking group that is covalently attached to the polymer particle. Frey, U.S. Pat. No. 4,581,337, incorporated herein by reference, discloses polyether polyamine linking agents that are: designed to be soluble in aqueous and organic solvents; chemically and thermal stable; chemically well-defined, so that reproducible results can be attained; and covalently attachable to amine-reactive groups on both the analyte and the surface of the polymer particle. These linking agents have the following structure:

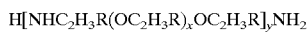

in which each R group can independently be —H or —CH$_3$ and can independently be bonded to either of the two carbon atoms; x is 0–70; and y is 1–20. Preferred linking agents are those in which x is 1–30; more preferred, those in which x is 1–15; and most preferred, those in which x is 1 or 2. Preferred linking agents are in which y is 1–10; preferred; and most preferred those in which y is 1–5. The polyether polyamines can be used as pure compounds, i.e., essentially all the molecules have the same value for x and y, or as mixtures of oligomers.

Polyether polyamine linking agents in which R is —H are preferred. Preferred polyether polyamine linking agents include: 1,8-diamino-3,6-dioxaoctane (DA-10); 1,10-diamino-4,7-dioxaoctane; 1,11-diamino-3,6,9-trioxaoctane; and 1,13-diamino-4,7,10-trioxaoctane. DA-10 is a more preferred linking agent.

These compounds can be prepared by procedures well-known to those skilled in the art. Frey, U.S. Pat. No. 4,581,337, for example, discloses preparation of polyether polyamines by reaction of the appropriate polyalkylene ether glycol with tosyl chloride in the presence of an acid acceptor, such as a tertiary amine, to form a tosylate ester, which is converted to the polyether polyamine by reaction with ammonia.

Provided that the analyte, analyte derivative, or analyte analog is not adversely affected, it can be covalently attached to the linking agent in any suitable solvent and, if necessary, under vigorous conditions because the polyether polyamine linking agents are soluble in many organic solvents, are oxidatively and thermally stable, and are not readily degraded by acidic or basic catalyst. Thus, analyte derivatives unsuitable for use in aqueous media, such as acid halides, acid anhydrides, allylic halides, α-haloketones, sulfonyl halides, and sulfonate esters, can be used to prepare the analyte-linker product (i.e., the conjugate). If necessary, before reaction with the linking agent, the analyte, analyte analog, or analyte derivative can be converted to an amine-reactive succinimidyl ester by reaction with disuccinimidyl carbonate.

Preparation of Functionalized Polymer Particles

The functionalized polymer particles can be prepared from the polymer particles by several different methods. The reaction between the conjugate and the polymer particle can be carried out either before, during, or after reaction of the polymer particle with the molecular surface modifier. These reactions can be carried out in aqueous media by procedures well known in the art. However, coupling can be carried out at more alkaline pH values than with analyte-protein conjugates. The preferred method is to attach both the molecular surface modifier and the conjugate at the same time.

The surface coverage of the polymer particle and the ratio of conjugate to molecular surface modifier can be controlled by varying the stoichiometry, reaction time, and the concentration of (1) the conjugate, (2) the molecular surface modifier, and (3) the polymer particles. Although more complete coverage typically increase agglutination rates, lesser coverage can increase the sensitivity of the assay.

The starting polymer latex should be about 3–25% by weight polymer particles, preferably 6–20% by weight polymer particles, more preferably 8–15% by weight polymer particles. The number of particles should be about $1 \times 10^{13}$ to $1 \times 10^{15}$ particles/mL of polymer latex, more preferably about $1 \times 10^{14}$ particles/mL of polymer latex. The concentration of conjugate should be about 50 to 50,000 molecules/particle, preferably 8,000 to 25,000 molecules/particle, more preferably 10,000 to 15,000 molecules/particle. Typically, the molar ratio of molecular surface modifier to conjugate should be in the range of about 10 to about 0.1; preferably about 5 to about 0.5; more preferably about 2. The amount of ionic surfactant in the reaction should be about 0.1% to 5%, preferably 0.5% to 2.0%. The temperature of the reaction should be about 60° C. to 90° C., preferably about 65° C. to 80° C., more preferably about 69° C. to 72° C. The pH of the reaction should be about 7.5 to 11.0, preferably 8.5 to 10.0, more preferably 9.0 to 9.5.

Stabilized Particle Reagent

The functionalized polymer particles can be suspended in a substantially aqueous medium, which can contain buffer, serum components and surfactants, to produce an immunologically active, stabilized particle reagent for use in a light scattering immunoassay. The stabilized particle reagent typically comprises from about 1 percent by weight to about 10 percent by weight functionalized polymer particles. The agglutination reaction can sometimes be accelerated by materials such as poly(ethylene glycol). In some cases, it may also be desirable to add a reducing agent, such as dithioerythritol, to reduce serum interferences. Sacrificial substances, such as serum albumin, may be added to coat active surfaces or be a substrate for oxidative or reductive chemical processes, frequently of unknown origin.

The particle reagent can be characterized by its A340/A600 ratio (ratio of the absorbance of the polymer latex at 340 nm to the absorbance of the latex at 600 nm), which is dependent on particle size. This ratio, which has a range of 10–13 for particles of 75 nm, indicates the amount of particle agglomeration. Larger particles have a lower limit that is less than 10.

A polymer latex with a ratio of less than 10 is unsatisfactory for use in a particle-enhanced turbidimetric-inhibition immunoassay. Preferably the reaction to covalently attach the analyte to the surface of the particle should not change this ratio, indicating that dimer formation has not taken place during attachment.

Assay

The particle reagent is used in a particle-enhanced turbidimetric-inhibition immunoassay (PETINIA). Addition of an antibody specific for the analyte attached to the particle causes the particles to aggregate. As the aggregates become large enough to scatter light, the suspension becomes turbid and the apparent optical density of the suspension increases. In a typical analysis the concentration of particles is adjusted so that the apparent optical density increases from about 1.0 to about 2.0 during the analysis. The stabilized particle reagent is typically diluted 25–100 fold to prepare the reagent used in the assay.

When a sample containing analyte and antibody is added to the particle reagent, the unbound analyte in the sample competes for the antibody with the particle-bound analyte. Both the rate and extent of aggregation are inhibited, providing a basis for quantifying the amount of analyte in the sample.

The wavelength that provides maximum sensitivity increases as the size of the particles increases. Because of light absorption by proteins and other components of biological fluids, the analysis should be carried out at a wavelength greater than about 320 nm. A convenient wavelength for analysis of particles that have a diameter of about 75 nm is 340 nm. Use of a longer wavelength to analyze particles in this size range reduces the sensitivity of the analysis.

Several different methods of measuring light scattering, such as nephelometry, particle counting, quasi-elastic light scattering, autocorrelation spectroscopy, and measurements of the dissymetry or polarization can be used. A preferred method is to measure the turbidity of the particle reagent because no special equipment, other than a spectrophotometer, which is generally available in clinical laboratories, is required. As aggregates form, the analyzing light is scattered and the apparent optical density of the reagent increases. The assay can be performed manually or it can be adapted to a variety of automated or semi-automated instruments, such as the aca® clinical analyzer and the Dimensions® clinical analyzer (Dale International Inc., Newark, Del.).

The inhibition immunoassay requires, in addition to the particle reagent, a bi- or multifunctional agglutinating agent to cause agglutination of the particle reagent. The agglutinating agent can be an antibody to the analyte, or a functionalized polymer particle in which the antibody is covalently attached to the particle. The agglutinating agent can also be an antibody to the analyte, covalently bonded to the linking agent.

Several different assay methods can be used for the measurement of analytes. In one method, the functionalized polymer particles contain the analyte, or a suitable derivative or analog of the analyte. Inhibition of agglutination by the free analyte is determined. In another method, both antibody containing and analyte containing particle reagents are present. Analyte inhibition is carried out in a competitive or sequential mode.

INDUSTRIAL APPLICABILITY

The functionalized polymer particles, the stabilized particle reagent, and the light scattering immunoassay of this invention can be used in the measurement of a variety of materials of biological interest. These include a wide variety of substances in biological fluids, cell and tissue extracts for which an immunological counter reactant can be produced, especially various drugs and drug metabolites as well as substances for which a quantitative determination is required for the assessment of a disease state.

The advantageous properties of this invention can be observed by reference to the following examples which illustrate, but do not limit, the invention.

EXAMPLES

| Glossary | |
| --- | --- |
| DA-10 | 2-[2-(2-Aminoethoxy)ethoxy]ethylamine; 1,8-diamino-3,6-dioxaoctane [$H_2N(CH_2CH_2O)_2CH_2CH_2NH_2$] |
| Gafac ® RE-610 surfactant | Anionic surfactant (GAF Corp.; now available from Rhone Poulenc, Collegeville, PA, as Rhodafac ® RE-610 surfactant) |
| Lidocaine | 2-(Diethylamino)-N-(2,6-dimethylphenyl)-acetamide |
| MA-10 | 2-[2-(2-Aminoethoxy)ethoxy]ethanol; [$H_2N(CH_2CH_2O)_3H$] |
| Procainamide | N-(2-diethylamino)benzamide |
| TFA PROC | N-Trifluoroacetyl procainamide; p-trifluoroacetamido-N-(2-diethylamino)-benzamide |

EXAMPLE 1

This example compares the difference in stability between particles that contain DA-10 and MA-10.

Polymer Latex

The polymer latex was an aqueous dispersion of polymer particles that consist of a core of poly(styrene) and a shell prepared from 95% by volume glycidyl methacrylate and 5% by volume ethylene glycol dimethacrylate, prepared as described in Craig, U.S. Pat. No. 4,488,042. The polymer latex contained 10.04% by weight solids. The A340/A600 ratio of the polymer latex was 12.70. The particles had an average diameter of 75.6 nm. Particle diameter was measured by quasi-electric light scattering on a Leeds and Northrup analyzer.

Stock Solutions

The following stock solutions were prepared.

Solution 1. Reaction Coupling Buffer. An aqueous solution that was 100 mmolar in sodium bicarbonate was prepared by diluting sodium bicarbonate with water. The coupling buffer is added to the reaction to keep the pH at about 9.3 so that the amines on the conjugate are not completely protonated and some are free to react with the epoxide groups on the shell of the latex particles.

Solution 2. Conjugate Solution. TFA-PROC (51.9 mg) dissolved in 3 mL of dimethyl sulfoxide.

Solution 3. Molecular Surface Modifier Solution. MA-10 (37.2 mg) dissolved in 2.500 mL of water.

Solution 4. DA-10 Solution. DA-10 (37.4 mg) dissolved in 2.500 mL of water.

Solution 5. Surfactant Solution. Essentially neutral 10% (weight/volume) Gafac® RE-610 surfactant was prepared by diluting the surfactant in a beaker with distilled water and adding concentrated sodium hydroxide until the pH was just above 7.0.

Coupling Reaction

A series of reagents was prepared. The solutions indicated in Table 1 were added to a series of centrifuge tubes, each of which contained 2.000 mL of particle latex and 1.500 mL of coupling buffer.

TABLE 1

| Sample | Solution Added (mL)[a] | | | | Water | Final Volume (mL) |
|---|---|---|---|---|---|---|
| | 1 | 2 | 3 | 4 | | |
| A | 0.314 | 0.294 | 0 | 0.340 | 2.000 | 6.448 |
| B | 0.314 | 0.147 | 0 | 0.340 | 2.000 | 6.301 |
| C | 0.251 | 0.294 | 0 | 0.340 | 2.000 | 6.385 |
| D | 0.251 | 0.147 | 0 | 0.340 | 2.000 | 6.238 |
| E | 0.189 | 0.147 | 0 | 0.340 | 2.000 | 6.176 |
| F | 0.314 | 0 | 0.294 | 0.310 | 2.000 | 6.661 |
| G | 0.314 | 0 | 0.147 | 0.310 | 2.000 | 6.514 |
| H | 0.251 | 0 | 0.294 | 0.310 | 2.000 | 6.598 |
| J | 0.251 | 0 | 0.147 | 0.310 | 2.000 | 6.451 |
| K | 0.189 | 0 | 0.147 | 0.310 | 2.000 | 6.389 |

[a]Each sample container initially contained 2.000 mL of particle latex and 1.500 mL of coupling buffer.

After the solutions were added, the ingredients were mixed by brief vortexing. Each container was sealed and heated for 18 hr at 70° C.

Evaluation

The absorbance of each sample was measured at 340 nm and 600 nm. Table 2 indicates the number of conjugate molecules per particle, the number of molecules of MA-10 or DA-10 per particle, and the A340/A600 ratio for each sample.

TABLE 2

| Sample | TFA-PROC[a] | MA-10[b] | DA-10[c] | A340[d] | A600[e] | A340/A600 |
|---|---|---|---|---|---|---|
| A | 10,000 | 20,020 | 0 | 2.780 | 0.223 | 12.5 |
| B | 10,000 | 10,010 | 0 | 2.780 | 0.251 | 11.1 |
| C | 8,000 | 20,020 | 0 | 2.482 | 0.211 | 11.8 |
| D | 8,000 | 10,010 | 0 | 2.560 | 0.216 | 11.9 |
| E | 6,024 | 10,010 | 0 | 2.840 | 0.225 | 12.6 |
| F | 10,000 | 0 | 20,000 | 2.240 | 0.199 | 11.3 |
| G | 10,000 | 0 | 10,000 | 2.251 | 0.223 | 10.1 |
| H | 8,000 | 0 | 20,000 | 2.540 | 0.223 | 11.4 |
| J | 8,000 | 0 | 10,000 | 2.470 | 0.211 | 11.7 |
| K | 6,024 | 0 | 10,000 | 2.520 | 0.212 | 11.9 |

[a]Molecules of TFA-PROC/polymer particle.
[b]Molecules of MA-10/polymer particle.
[c]Molecules of DA-10/polymer particle.
[d]Absorbance at 340 nm.
[e]Absorbance at 600 nm.

In each case the sample in which MA-10 was used had a higher A340/A600 than the corresponding sample in which DA-10 was used.

EXAMPLE 2

This example illustrates the increase on stability achieved with an increasing concentration of molecular surface modifier at constant conjugate concentration.

The polymer latex contained polymer particles that consist of a poly(styrene) core overcoated with crosslinked poly(glycidyl methacrylate), prepared as described in Craig, U.S. Pat. No. 4,480,042. The polymer latex contained 10.04% by weight solids. The particles had an average diameter of 75.6 nm. The A340/A600 ratio was 12.70. The functionalized polymer particles were prepared by the same general procedure as Example 1. The conjugate solution was made by dissolving 611.1 mg of lidocaine hydrochloride in 30 mL of water. The molecular surface modifier solution was prepared by dissolving 74.4 mg of MA-10 in 5.00 mL of water (11.88 mg/mL). No DA-10 solution was used in this Example.

A series of stabilized particle reagents was prepared by adding 2.00 mL of the polymer latex, 4.00 mL of coupling buffer, 0.200 mL of conjugate solution, 0.350 mL of surfactant solution, and the reagents indicated in Table 3 to a series of centrifuge tubes.

TABLE 3

| Sample | MA-10[a](mL) | Water (mL) | Final Volume (mL) |
|---|---|---|---|
| A | 0.400 | 0.000 | 6.95 |
| B | 0.340 | 0.060 | 6.95 |
| C | 0.289 | 0.111 | 6.95 |
| D | 0.246 | 0.154 | 6.95 |
| E | 0.209 | 0.191 | 6.95 |
| F | 0.177 | 0.223 | 6.95 |
| G | 0.151 | 0.249 | 6.95 |
| H | 0.128 | 0.272 | 6.95 |
| J | 0.109 | 0.291 | 6.95 |
| K | 0.093 | 0.307 | 6.95 |
| L | 0.079 | 0.321 | 6.95 |
| M | 0.067 | 0.333 | 6.95 |
| N | 0.057 | 0.343 | 6.95 |
| P | 0.048 | 0.352 | 6.95 |
| Q | 0.041 | 0.359 | 6.95 |
| R | 0.035 | 0.365 | 6.95 |

[a]11.88 mg of MA-10/mL.

After the solutions were added, the ingredients were mixed by brief vortexing. Each container was sealed and heated for 18 hr at 70° C.

The absorbance of each sample was measured at 340 nm and 600 nm. Table 4 indicates the number of conjugate molecules per particle, the number of molecules of molecular surface modifier per particle, and the A340/A600 ratio for each sample.

TABLE 4

| Sample | LIDO[a] | MA-10[b] | A340[c] | A600[d] | A340/A600 | C/M[e] |
|---|---|---|---|---|---|---|
| A | 10,000 | 27,238 | 1.246 | 0.108 | 11.54 | 0.37 |
| B | 10,000 | 23,152 | 1.223 | 0.106 | 11.54 | 0.43 |
| C | 10,000 | 19,680 | 1.205 | 0.107 | 11.26 | 0.51 |
| D | 10,000 | 16,728 | 1.200 | 0.108 | 11.11 | 0.60 |
| E | 10,000 | 14,219 | 1.244 | 0.109 | 11.41 | 0.70 |
| F | 10,000 | 12,086 | 1.204 | 0.106 | 11.36 | 0.83 |
| G | 10,000 | 10,273 | 1.200 | 0.107 | 11.21 | 0.97 |
| H | 10,000 | 8,732 | 1.270 | 0.112 | 11.34 | 1.15 |
| J | 10,000 | 7,422 | 1.250 | 0.110 | 11.36 | 1.35 |
| K | 10,000 | 6,309 | 1.240 | 0.111 | 11.17 | 1.59 |
| L | 10,000 | 5,363 | 1.243 | 0.111 | 11.20 | 1.86 |
| M | 10,000 | 4,558 | 1.242 | 0.123 | 10.10 | 2.19 |
| N | 10,000 | 3,874 | 1.260 | 0.124 | 10.16 | 2.58 |
| P | 10,000 | 3,293 | 1.311 | 0.130 | 10.08 | 3.03 |
| Q | 10,000 | 2,799 | 1.333 | 0.131 | 10.18 3 | 0.57 |
| R | 10,000 | 2,379 | 1.260 | 0.125 | 10.08 | 4.20 |

[a]Molecules of lidocaine hydrochloride/polymer particle.
[b]Molecules of MA-10/polymer particle.
[c]Absorbance at 340 nm.
[d]Absorbance at 600 nm.
[e]Rato of conjugate to molecular surface modifier.

For samples that contain 10,000 conjugate molecules per functionalized polymer particle, the A340/A600 ratio increase when the number of particles of MA-10 per particle increases. The ratio increases significantly when the ratio of conjugate to molecular surface modifier is less than 2.

EXAMPLE 3

This example illustrates the increase on stability achieved with a constant concentration of molecular surface modifier and an increasing concentration of conjugate.

The general procedure of Example 2 was repeated except that the conjugate solution was prepared by dissolving 180 mg of procainamide hydrochloride in 15 mL of water and the molecular surface modifier solution was prepared by adding 38 mg of MA-10 to 2.5 mL of water.

A series of stabilized particle reagents was prepared by adding 2.00 mL of the polymer latex, 2.50 mL of coupling buffer, 0.102 mL of molecular surface modifier solution, 0.320 mL of surfactant solution, and the reagents indicated in Table 5 to a series of centrifuge tubes. The concentration of conjugate was purposely kept very high and ranged from 7.0 mM to 1.44 mM. A conjugate concentration of 7.0 mM, or higher, would normally agglomerate the particles in the absence of a molecular surface modifier.

TABLE 5

| Sample | Conjugate (mL) | Water (mL) | Final Volume (mL) |
|---|---|---|---|
| A | 1.023 | 0.375 | 6.32 |
| B | 0.921 | 0.477 | 6.32 |
| C | 0.829 | 0.569 | 6.32 |
| D | 0.746 | 0.652 | 6.32 |
| E | 0.671 | 0.727 | 6.32 |
| F | 0.604 | 0.794 | 6.32 |
| G | 0.544 | 0.854 | 6.32 |
| H | 0.489 | 0.909 | 6.32 |
| J | 0.440 | 0.958 | 6.32 |
| K | 0.396 | 1.002 | 6.32 |
| L | 0.357 | 1.041 | 6.32 |
| M | 0.321 | 1.077 | 6.32 |
| N | 0.289 | 1.109 | 6.32 |
| P | 0.260 | 1.138 | 6.32 |
| Q | 0.234 | 1.164 | 6.32 |
| R | 0.211 | 1.187 | 6.32 |

[a]180 mg of procainamide hydrochloride in 15 mL of water.

After the solutions were added, the ingredients were mixed by brief vortexing. Each container was sealed and heated for 18 hr at 70° C.

The absorbance of each sample was measured at 340 nm and 600 nm. Table 6 indicates the number of conjugate molecules per functionalized polymer particle, the number of molecules of molecular surface modifier per particle, the A340/A600 ratio for each sample, and the ratio of conjugate to molecular surface modifier for each sample.

TABLE 6

| Sample | PROC[a] | MA-10[b] | A340[c] | A600[d] | A340/A600 | C/M[e] |
|---|---|---|---|---|---|---|
| A | 30,837 | 7,195 | 1.937 | 0.298 | 6.50 | 4.29 |
| B | 27,754 | 7,195 | 1.586 | 0.206 | 7.70 | 3.86 |
| C | 24,978 | 7,195 | 1.210 | 0.139 | 8.70 | 3.47 |
| D | 22,480 | 7,195 | 1.100 | 0.144 | 9.65 | 3.12 |
| E | 20,232 | 7,195 | 1.715 | 0.162 | 10.59 | 2.81 |
| F | 18,209 | 7,195 | 1.686 | 0.151 | 11.17 | 2.53 |
| G | 16,388 | 7,195 | 1.740 | 0.152 | 11.45 | 2.28 |
| H | 14,749 | 7,195 | 1.584 | 0.140 | 11.31 | 2.05 |
| J | 13,274 | 7,195 | 1.540 | 0.132 | 11.68 | 1.84 |
| K | 11,947 | 7,195 | 1.570 | 0.135 | 11.63 | 1.66 |
| L | 10,752 | 7,195 | 1.562 | 0.136 | 11.48 | 1.49 |
| M | 9,677 | 7,195 | 1.540 | 0.133 | 11.58 | 1.34 |
| N | 8,709 | 7,195 | 1.510 | 0.132 | 11.44 | 1.21 |
| P | 7,838 | 7,195 | 1.571 | 0.137 | 11.47 | 1.09 |
| Q | 7,055 | 7,195 | 1.552 | 0.136 | 11.41 | 0.98 |
| R | 6,349 | 7,195 | 1.580 | 0.140 | 11.29 | 0.88 |

[a]Molecules of procainamide hydrochloride/polymer particle.
[b]Molecules of MA-10/polymer particle.
[c]Absorbance at 340 nm.
[d]Absorbance at 600 nm.
[e]Rato of conjugate to molecular surface modifier.

Having described the invention, I now claim the following and their equivalents:

1. A particle for use in a light scattering immunoassay, said particle having an inner core and outer shell and comprising:
   a conjugate attached to the outer surface; and,
   at least one MSM attached to the outer surface and having the structure:

$R(OCH_2CH_2)_nNH_2$ wherein R is —H, —CH$_3$ or —CH$_2$CH$_3$ and n is an integer between 2 and 10, inclusive, whereby an electrostatically neutral environment unable to immobilize drug analogs is provided at one end of the MSM.

2. The polymer particle of claim 1 in which the amine-reactive group is an epoxide.

3. The polymer particle of claim 2 in which n is an integer between 2 and 6, inclusive.

4. The polymer particle of claim 3 in which R is hydrogen.

5. The polymer particle of claim 4 in which n is an integer between 3 and 5, inclusive.

6. The polymer particle of claim 5 in which said functionalized polymer particle has a diameter of 60 to 80 nm.

7. The particle of claim 5 in which the conjugate is selected from the group consisting of lidocaine, procainamide, N-trifluoroacetal procainamide, quinidine, cyclosporin, and an amine conjugate selected from the group consisting of valproic acid, digoxin and digoxigenin.

8. The polymer particle of claim 1 in which said conjugate is an analyte, analyte derivative, or analyte analog directly covalently bonded to said polymer particle.

9. The polymer particle of claim 8 in which the amine-reactive group is an epoxide.

10. The polymer particle of claim 9 in which n is an integer between 2 and 6, inclusive.

11. The polymer particle of claim 10 in which R is hydrogen.

12. The polymer particle of claim 11 in which n is an integer between 3 and 5, inclusive.

13. A stabilized particle reagent suitable for use in a light scattering immunoassay, said reagent comprising polymer particles suspended in a substantially aqueous medium, said particle having an inner core and outer shell and comprising:
   a conjugate attached to the outer surface; and,
   at least one MSM attached to the outer surface and having the structure:

$R(OCH_2CH_2)_nNH_2$ wherein R is —H, —CH$_3$ or —CH$_2$CH$_3$ and n is an integer between 2 and 10, inclusive, whereby an electrostatically neutral environment unable to immobilize drug analogs is provided at one end of the MSM.

14. The stabilized particle reagent of claim 13 in which the amine-reactive group is an epoxide.

15. The stabilized particle reagent of claim 14 in which n is an integer between 2 and 6, inclusive.

16. The stabilized particle reagent of claim 15 in which R is hydrogen.

17. The stabilized particle reagent of claim 16 in which n is an integer between 3 and 5, inclusive.

18. The stabilized particle reagent of claim 13 in which said conjugate is an analyte, analyte derivative, or analyte analog directly covalently bonded to said polymer particle.

19. The stabilized particle reagent of claim 18 in which the amine-reactive group is an epoxide.

20. The stabilized particle reagent of claim 19 in which n is an integer between 2 and 6, inclusive.

21. The stabilized particle reagent of claim 20 in which R is hydrogen.

22. The stabilized particle reagent of claim 21 in which n is an integer between 3 and 5, inclusive.

23. The stabilized particle reagent of claim 22 in which the conjugate is selected from the group consisting of lidocaine, procainamide, N-trifluoroacetal procainamide, quinidine, cyclosporin, and an amine conjugate selected from the group consisting of valproic acid, digoxin and digoxigenin.

24. The stabilized particle reagent of claim 13 in which said functionalized polymer particles comprise 1 to 10 percent by weight of said stabilized particle reagent.

25. The stabilized particle reagent of claim 24 in which the amine-reactive group is an epoxide, R is hydrogen, and n is an integer between 3 and 5, inclusive.

26. The stabilized particle reagent of claim 25 in which said functionalized polymer particles have a diameter of 60 to 80 nm.

27. The stabilized particle reagent of claim 26 in which the conjugate is selected from the group consisting of lidocaine, procainamide, N-trifluoroacetal procainamide, quinidine, cyclosporin, and an amine conjugate selected from the group consisting of valproic acid, digoxin and digoxigenin.

28. The particle of claim 1 wherein the inner core is a polymer having a refractive index of at least 1.54.

29. The particle of claim 1 wherein the outer shell comprises, in polymerized form, an ethylenically unsaturated monomer having an amine-reactive group.

30. The particle of claim 29 wherein the outer shell further comprises one or more ethylenically unsaturated monomers in an amount sufficient to produce a water insoluble polymer.

31. The particle of claim 29 wherein the outer shell further comprises up to 10% by weight of a cross-linking monomer.

32. The particle reagent of claim 13 wherein the inner core is a polymer having a refractive index of at least 1.54.

33. The particle reagent of claim 13 wherein the outer shell comprises, in polymerized form, an ethylenically unsaturated monomer having an amine-reactive group.

34. The particle of claim 33 wherein the outer shell further comprises one or more ethylenically unsaturated monomers in an amount sufficient to produce a water insoluble polymer.

35. The particle reagent of claim 33 wherein the outer shell further comprises up to 10% by weight of a cross-linking monomer.

* * * * *